(12) United States Patent
Heyman

(10) Patent No.: US 8,949,136 B2
(45) Date of Patent: Feb. 3, 2015

(54) METHOD FOR ON-LINE PREDICTION OF MEDICAL DIAGNOSIS

(71) Applicant: Lee Jared Heyman, Marietta, GA (US)

(72) Inventor: Lee Jared Heyman, Marietta, GA (US)

( * ) Notice: Subject to any disclaimer, the term of this patent is extended or adjusted under 35 U.S.C. 154(b) by 199 days.

(21) Appl. No.: 13/646,413

(22) Filed: Oct. 5, 2012

(65) Prior Publication Data

US 2013/0030832 A1 Jan. 31, 2013

Related U.S. Application Data

(63) Continuation-in-part of application No. 12/619,256, filed on Nov. 16, 2009, now Pat. No. 8,285,632.

(60) Provisional application No. 61/114,700, filed on Nov. 14, 2008.

(51) Int. Cl.
*G06Q 50/22* (2012.01)
*G06F 19/00* (2011.01)
*G06Q 10/10* (2012.01)

(52) U.S. Cl.
CPC .............. *G06Q 50/22* (2013.01); *G06F 19/34* (2013.01); *G06Q 10/10* (2013.01)
USPC ............................................................. 705/2

(58) Field of Classification Search
CPC G06F 19/345; G06F 19/3425; G06F 19/3443
USPC ............................................................. 705/2
See application file for complete search history.

(56) References Cited

U.S. PATENT DOCUMENTS

| | | | |
|---|---|---|---|
| 8,864,663 B1 | 10/2014 | Kahn et al. | |
| 2006/0242109 A1* | 10/2006 | Pereira et al. | 707/1 |
| 2012/0173273 A1* | 7/2012 | Ashford | 705/2 |
| 2012/0245952 A1* | 9/2012 | Halterman et al. | 705/2 |
| 2013/0238647 A1* | 9/2013 | Thompson | 707/758 |

* cited by examiner

*Primary Examiner* — Jessica Lemieux
(74) *Attorney, Agent, or Firm* — Bryan W. Bockhop; Bockhop & Associates, LLC

(57) ABSTRACT

In a method of generating a diagnosis of a medical condition, a list of symptoms is received at a server from a patient computer. The list of symptoms is presented to a plurality of participants. A list of diagnoses corresponding to the list of symptoms is presented to the plurality of participants. An input is received from each of the plurality of participants in which the input indicates a likelihood of each of the potential diagnoses being correct. The input from each of the plurality of participants is averaged, thereby generating a ranking of the potential diagnoses from highest likelihood of being correct to lowest likelihood of being correct, which is transmitted to the patient. An indication of which diagnosis was found to be correct is received from the patient. A reward is paid to each participant based on how likely the participant indicated that the correct diagnosis was correct.

8 Claims, 24 Drawing Sheets

FIG. 3A iCE - Internal Test

*Trading Tutorial*

A major soft drink company recently tested several new soda ideas on a test panel in the United States. Your job is to predict which ideas were liked the most with this stock trading game we'll present you with the new soda ideas they tested, complete with images and description. Once you've ranked each concept, you're the given the opportunity to buy virtual "shares" in the concepts using $1 USD value Trading Dollars (VTD) balance and the trading fees below. When the round closes, you'll be given a top VTD payout for each share you spent on the soda idea that actually sold the most to the test studies. Any shares your own in the other concepts will become worthless. Your objective is to maximize your total balance, once every $10.00 versus Trading Dollars you may continue trading.

- You must invest at least 80% of your balance to continue.
- You can only buy shares in one concept at a time, but as long as you have a sufficient virtual Trading Dollar balance you may continue trading.

| Concepts | Current Price | Shares | Virtual Dollars to Invest | | Your Cost | New Price |
|---|---|---|---|---|---|---|
| Cherry | $7.00 | 0 | | 100% | $0.00 | $7.00 |
| Grape | $20.91 | 0 | | 100% | $0.00 | $20.91 |
| Lemon | $14.16 | 0 | | 100% | $0.00 | $14.16 |
| Lime | $40.54 | 0 | | 100% | $0.00 | $40.54 |
| Orange | $10.70 | 0 | | 100% | $0.00 | $10.70 |

[Buy Now]

Today, we'd like for you to participate in a new type of survey exercise that's designed to do something remarkable: save lives. We'll first ask you about your experience with different types of diseases and conditions, and then provide you with the opportunity to help diagnose a difficult medical case. Don't worry, you don't need a PhD to participate. We believe in the power of groups to gather information and make wise decisions, so your input will be weighed with others in order to provide clues for solving the case.

This exercise is an experiment in the power of collective intelligence and collaboration for good. Your input will be used to improve diagnostics and quality of life for patients suffering from complex illnesses than are difficult to diagnose.

Would you like to participate?

○ Yes
○ No

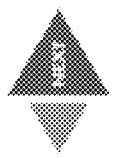

FIG. 4A

Your Experience

In order to assign you to the most appropriate case, we'd like to ask you a few questions about yourself.

Do you have experience with any of the following illnesses, either personally or through a close friend or family member?

- ☐ Depression
- ☐ Multiple Sclerosis
- ☐ Alzheimer's disease
- ☒ Fragile X syndrome
- ☐ Osteoporosis
- ☐ Female hormonal imbalance
- ☐ None of the Above Do you work in any of the following industries?

- ☐ Agriculture, Mining
- ☐ Construction
- ☐ Finance, Insurance, Real Estate
- ☐ Government
- ☒ Health Care
- ☐ Internet
- ☐ Manufacturing
- ☐ Retail, Wholesale
- ☐ Services
- ☐ Transportation
- ☐ Communications, Utilities
- ☐ Nonprofit
- ☐ None of the above

FIG. 4B

Background

Great, we need your input! Here's the case. Once you have reviewed the information, click "Next" to continue.

The patient is an 18-year-old female. Recently she began to experience the following symptoms:

- moderate psychological depression
- irregular menstrual cycles

She is otherwise healthy, except for the following, which existed prior to the onset of her recent symptoms:

- seasonal allergies
- attention deficit disorder (ADD)
- tonsillectomy when she was younger The genetic disorder Fragile X Syndrome runs in her family, and through genetic testing she has been identified as a pre-mutation carrier of the gene responsible for this disorder. Her mother is also a pre-mutation carrier and her brother is fully expressive of Fragile X.

She has visited psychologists and psychiatrists for treatment of her depression, and neither psychological counseling nor anti-depressant medications have relieved her symptoms.

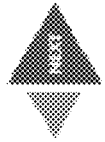

FIG. 4C

The Diagnosis

Introduction to Diagnosis Recommendation:

Your job is to recommend a possible diagnosis for the patient. You may draw on your experience with the conditions stated, look up information on other websites, use reference materials, or even ask for the opinions of friends and family to help you make your recommendation.

In addition, you'll be able to see recommendations made by other participants in this study. If you agree with a possible diagnosis, you may express your approval by giving it a "thumbs up". If you disagree with a recommendation, you can give it a thumb's down.

Remember, your information does not need to be perfect. Collectively, we can solve this case!

When you're ready to submit your ideas, please click "Next".

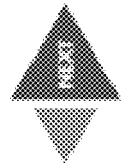

FIG. 4D

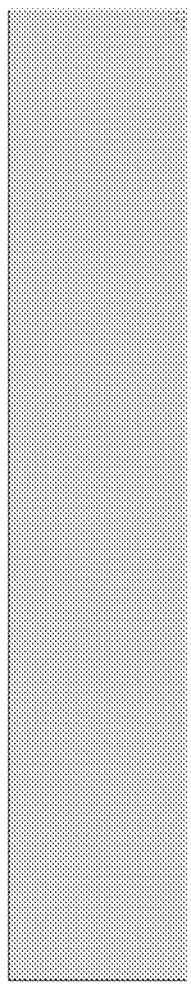
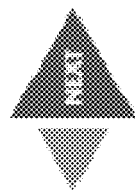
FIG. 4F

About You

Thank you for your contribution! Now, we'd like to ask you a few questions about yourself. Your responses will be used strictly for classification purposes.

What is your age?

○ 18-24
○ 25-29
○ 30-34
○ 35-39
○ 40-44
○ 45-49
○ 50-54
⊙ 55+

What is your gender?

⊙ Male
○ Female

Today, we'd like for you to participate in a new type of survey exercise that's designed to do something remarkable: save lives. We'll first ask you about your experience with different types of diseases and conditions, and then provide you with the opportunity to help diagnose a difficult medical case. In addition to the reward you'll be receiving for participating, by investing in the correct diagnosis, you'll be able to earn up to an additional $10!

This exercise is an experiment in the power of collective intelligence and collaboration for good. Your input will be used to improve diagnostics and quality of life for patients suffering from complex illnesses that are difficult to diagnose.

Would you like to participate?

○ Yes
○ No

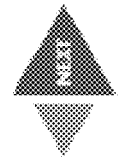

FIG. 4H

Potential Diagnoses

Major Depression

Premature Menopause

General Anxiety Disorder

Fragile X Associated Primary Ovarian Insufficiency (FXPOI)

Hypothyroidism

METHOD FOR ON-LINE PREDICTION OF MEDICAL DIAGNOSIS

CROSS-REFERENCE TO RELATED APPLICATION(S)

This application claims the benefit of U.S. Provisional Patent Application Ser. No. 61/114,700, filed Nov. 14, 2008, the entirety of which is hereby incorporated herein by reference.

This application is a continuation-in-part of, and claims the benefit of, U.S. patent application Ser. No. 12/619,256, filed Nov. 16, 2009, which issued as U.S. Pat. No. 8,285,632 on Oct. 9, 2012, the entirety of which is hereby incorporated herein by reference.

BACKGROUND OF THE INVENTION

1. Field of the Invention

The present invention relates to methods of diagnosing medical conditions and, more specifically, to a method of diagnosing medical conditions employing a prediction market approach.

2. Description of the Related Art

Currently, conducting a scientifically sound new product or marketing concept test can be an expensive endeavor. Professionally designed concept tests can cost upwards of $6-8,000 per concept tested, and a single focus group can cost around $12,000. Since this is outside the reach of many marketers and small business owners, they instead often must rely upon their own intuition or the opinions of a few friends or colleagues.

Medical diagnoses, especially for infrequently-encountered conditions, can sometimes be difficult for a single practitioner to achieve accurately. In some cases, many different types of individuals will have familiarity with symptoms relating to such conditions. While each individual might have useful insight, sometimes it is difficult to identify a single individual who has a correct understanding of such a condition. Thus, trying to get a correct diagnosis can be time consuming and expensive.

A need, therefore, exists for an accurate and more economical way to diagnose medical conditions.

SUMMARY OF THE INVENTION

In general, embodiments of the present invention provide an improvement by, among other things, providing an innovative, high-tech system and method that presents a new and highly accurate way to predict the success of new products, packages, logos, advertisements and anything else traditionally measured with monadic concept tests or traditional screening methodologies.

In particular, embodiments of the present invention provide an online marketplace where users are given virtual dollars to buy "shares" in the product concepts (e.g., products, packages logos, advertisements, etc.) that a merchant wishes to test. Just like in the real world markets, share prices may fluctuate based on the perceived market value of the underlying asset. By observing how share prices move over time, embodiments of the present invention enable accurate predictions regarding the real world success of the concepts being tested.

In accordance with one aspect, a method is provided for conducting a prediction market to test product concepts. In one embodiment, the method may include: (1) receiving a selection of one or more markets in which a user would like to participate in a prediction market; (2) retrieving information associated with a group of product concepts falling within one of the selected markets, said information comprising a stock price associated with respective product concepts of the group of product concepts; (3) causing the retrieved information to be displayed; (4) receiving an indication of a number of shares to be purchased by the user in at least one of the product concepts; and (5) adjusting, by a processor, the stock price associated with each product concept in the group of product concepts based at least in part on the number of shares purchased, wherein a sum of the stock prices associated with each of the product concepts in the group of product concepts is constant.

According to another aspect, a network entity is provided for conducting a prediction market to test product concepts. In one embodiment, the network entity may include a processor configured to: (1) receive a selection of one or more markets in which a user would like to participate in a prediction market; (2) retrieve information associated with a group of product concepts falling within one of the selected markets, said information comprising a stock price associated with respective product concepts of the group of product concepts; (3) cause the retrieved information to be displayed; (4) receive an indication of a number of shares to be purchased by the user in at least one of the product concepts; and (5) adjust the stock price associated with each product concept in the group of product concepts based at least in part on the number of shares purchased, wherein a sum of the stock prices associated with each of the product concepts in the group of product concepts is constant.

In accordance with yet another aspect, a computer program product is provided for conducting a prediction market to test product concepts. The computer program product contains at least one computer-readable storage medium having computer-readable program code portions stored therein. The computer-readable program code portions of one embodiment may include: (1) a first executable portion for receiving a selection of one or more markets in which a user would like to participate in a prediction market; (2) a second executable portion for retrieving information associated with a group of product concepts falling within one of the selected markets, said information comprising a stock price associated with respective product concepts of the group of product concepts; (3) a third executable portion for causing the retrieved information to be displayed; (4) a fourth executable portion for receiving an indication of a number of shares to be purchased by the user in at least one of the product concepts; and (5) a fifth executable portion for adjusting the stock price associated with each product concept in the group of product concepts based at least in part on the number of shares purchased, wherein a sum of the stock prices associated with each of the product concepts in the group of product concepts is constant.

The disadvantages of the prior art are overcome by the present invention which, in one aspect, is a method of generating a diagnosis of a medical condition, in which a list of symptoms is received at a server from a patient computer in communication with the global computer network. The list of symptoms is presented to a plurality of participants on a participant computer screen in data communication with the server. A list of potential diagnoses corresponding to the list of symptoms is presented to the plurality of participants on the participant computer screen. An input is received from the participant computer of each of the plurality of participants in which the input indicates a likelihood of each of the potential diagnoses being correct. The input from each of the plurality of participants regarding the likelihood of each of the potential diagnoses being correct is averaged at the server, thereby generating a ranking of the potential diagnoses from highest likelihood of being correct to lowest likelihood of being correct. The ranking is transmitted from the server to the patient computer. An indication of which of the potential diagnoses was found to be a correct diagnosis by a physician who examined the patient is received at the server from the patient computer. A reward is paid to each participant based on how likely the participant indicated that the correct diagnosis was correct.

In another embodiment, the invention includes a network entity that includes a plurality of participant computers in data communication with a global computer network and a server processor. The server processor is configured to retrieve information associated with a group of symptoms experienced by a patient; cause the retrieved information to be displayed on a plurality of computers operated by a corresponding plurality of participants; cause a plurality of diagnoses to be displayed on the plurality of computers; receive from each computer an indication from each participant of a likelihood that at least one diagnosis of the plurality of diagnoses has caused the group of symptoms; present to the patient a ranking of diagnoses based on the indication received from each participant; receive from the patient an identification of which diagnoses has been found to be correct; and reward each participant according to how closely the indication from the participant corresponds to the identification from the patient.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIGS. 3A-3K are screen shots illustrating an interface for conducting prediction markets in accordance with an embodiment described herein.

FIGS. 4A-4J are screen shots illustrating an interface for conducting medical diagnosis markets in accordance with an embodiment described herein.

DETAILED DESCRIPTION OF THE INVENTION

Figure 1A:
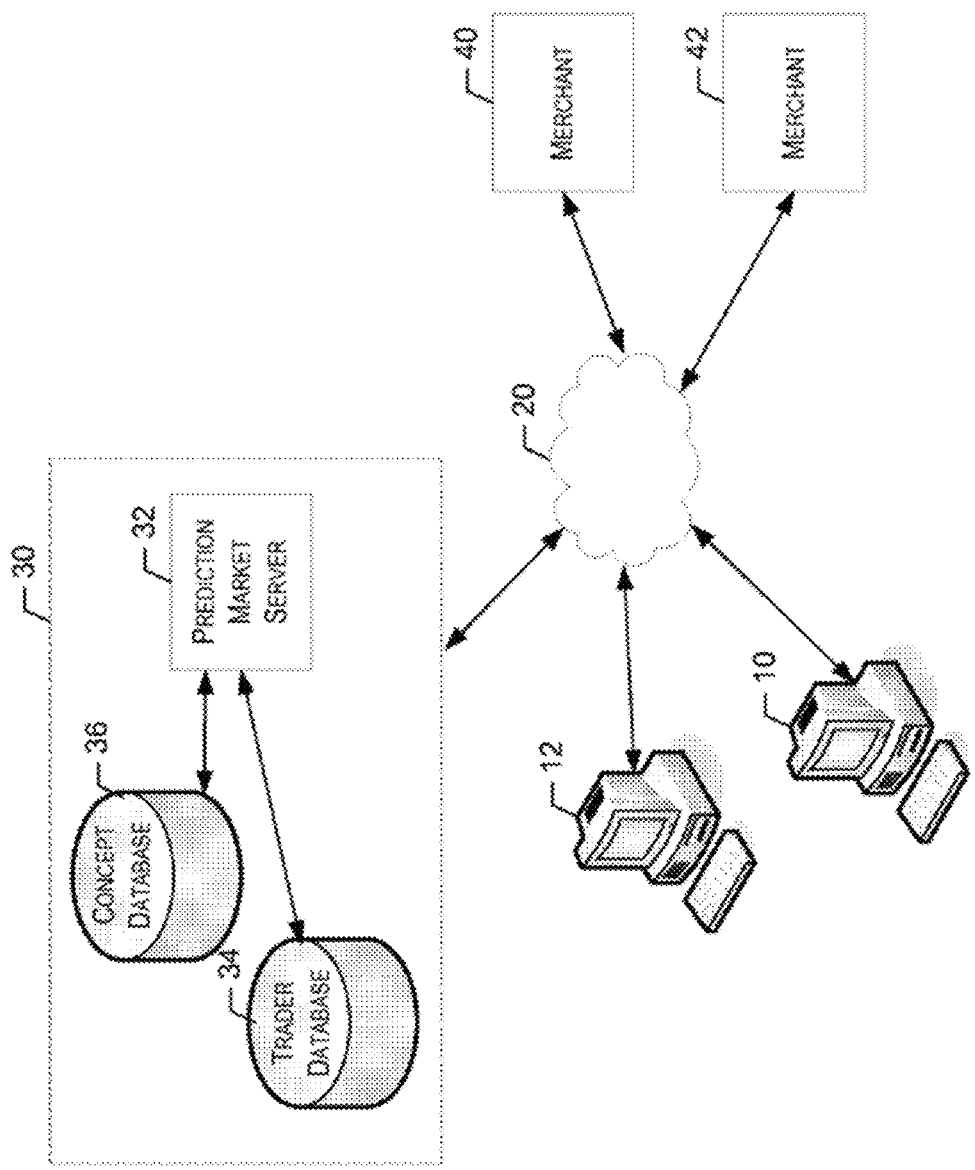
FIG. 1A is a block diagram of one type of system that would benefit from embodiments of the present invention

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on." Also, as used herein, "global computer network" includes the Internet.

Overall System and Prediction Market Server:

Referring to FIG. 1A, an illustration of one type of system that may benefit from embodiments of the present invention is provided. As shown in FIG. 1A, the system can include one or more user electronic devices (e.g., personal computers (PCs), laptops, personal digital assistants (PDAs), etc.) 10, 12 in communication with a Prediction Market system 30 over a communication network 20 (e.g., a wired or wireless personal area network (PAN), local area network (LAN), wide area network (WAN), a global computer network, etc.) for the purpose of enabling the users to participate in a prediction market for product concept testing. As described in more detail below, the users may further be in communication with the Prediction Market system 30 for the purpose of completing a survey, the results of which may be used to determine the outcome of a prediction market.

In one embodiment, the Prediction Market system 30 can include a Prediction Market server 32, or similar network entity, the functionality of which is described in more detail below with regard to FIGS. 1B and 2, as well as one or more databases 34, 46. The databases may include, for example, a trader database 34 configured to store information associated with each of a plurality of traders including, for example, a trader profile, a monetary balance of the trader, a record of the shares purchased and/or sold by the trader, as well as the stock price of those shares at the time of purchase or sale, and/or the like. The databases may further include a concept database 36 configured to store information associated with each of a plurality of product concepts corresponding to a plurality of different markets (e.g., apparel, electronics, etc.). As used herein "product concept," can refer to any product, package, logo, advertisement and/or the like that is capable of being tested for likely market success via a prediction market in the manner described herein.

The system may further include one or more merchant servers 40, 42, or similar network entities, also in communication with the Prediction Market system 30 over the same or different network 20. As described in more detail below, the merchant servers 40, 42 may be configured to provide information regarding product concepts to be tested via the Prediction Market system 30, as well as to receive feedback relating to the prediction markets conducted.

While the foregoing describes separate databases 34 and 36 as being associated with and containing information used by the Prediction Market system 30 and corresponding server 32, as one of ordinary skill in the art will recognize in light of this disclosure, the contents of these databases can be stored in a single database or spread over any number of databases. Alternatively, or in addition, some or all of the information described as being stored in the databases may be stored locally on the Prediction Market server 32.

In addition, while the foregoing refers to a Prediction Market "server" and merchant "servers," as one of ordinary skill in the art will recognize in light of this disclosure, embodiments of the present invention are not limited to a client-server architecture. In contrast, other similar computing devices and architectures may likewise be used without departing from the spirit and scope of embodiments described herein.

Figure 1B:
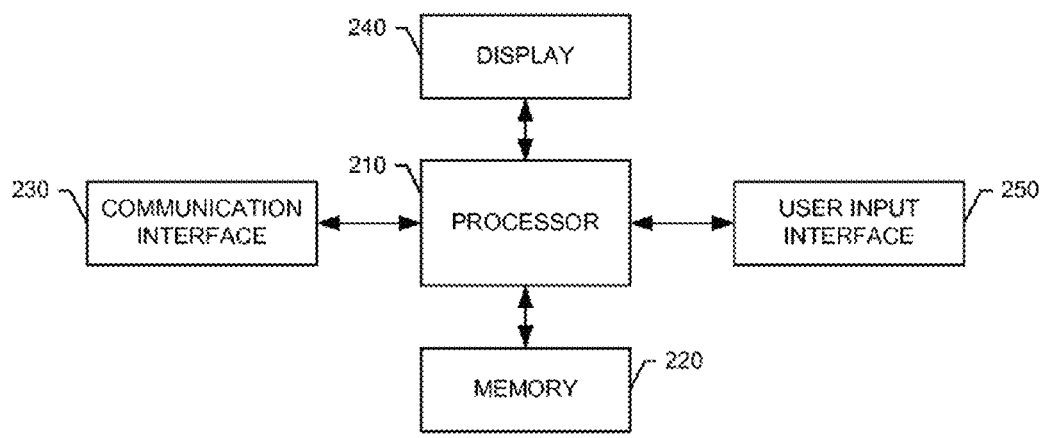
FIG. 1B is a schematic block diagram of an entity capable of operating as a Prediction Market server in accordance with embodiments of the present invention.

Referring now to FIG. 1B, a block diagram of an entity capable of operating as a Prediction Market server 32 is shown in accordance with one embodiment of the present invention. The entity capable of operating as a Prediction Market server 32 can include various means for performing one or more functions in accordance with embodiments of the present invention, including those more particularly shown and described herein. It should be understood, however, that one or more of the entities may include alternative means for performing one or more like functions, without departing from the spirit and scope of the present invention. As shown, the entity capable of operating as a Prediction Market server 32 can generally include means, such as a processor 210, for performing or controlling the various functions of the entity.

In particular, the processor 210 may be configured to perform the processes discussed in more detail below with regard to FIG. 2. For example, according to one embodiment the processor 210 may be configured to cause to be displayed information, including a stock price, associated with each of a group of product concepts for which a prediction market is being conducted. The processor 210 may further be configured to then receive an indication of a number of shares in one or more of the product concepts a trader would like to purchase, and to update the stock price associated with each of the product concepts in the group based on the shares being purchased. Once the prediction market has been closed, the processor 210 may be further configured to determine a winning product concept, cash out the traders participating in the prediction market, and generate and transmit a report associated with the prediction market to the merchant associated with the group of product concepts.

In one embodiment, the processor is in communication with or includes memory 220, such as volatile and/or non-volatile memory that stores content, data or the like. For example, the memory 220 may store content transmitted from, and/or received by, the entity. Also for example, the memory 220 may store software applications, instructions or the like for the processor to perform steps associated with operation of the entity in accordance with embodiments of the present invention. In particular, the memory 220 may store software applications, instructions or the like for the processor to perform the operations described above and below with regard to FIG. 2 for conducting a prediction market to test product concepts.

For example, according to one embodiment, the memory 120 may store one or more modules for instructing the processor 210 to perform the operations including, for example, a price adjustment module, a winning concept module, a cash out module, and an analysis module. In one embodiment, the price adjustment module may be configured to cause the processor 210 to adjust the price of each of the group of product concepts being tested based on the number of shares being purchased by a trader in at least one of the product concepts. The winning concept module may be configured to cause the processor 210 to identify which of the product concepts in the group of product concepts is the winning concept, and the cash out module may be configured to cause the processor 210 to determine an amount to be paid to or by the traders participating in the prediction market based on the winning concept, the number of shares purchased by each trader in the various product concepts, and the price of those shares at the time of purchase. Finally, the analysis module may be configured to cause the processor 210 to analyze the results of the prediction market in order to generate and transmit a report to the merchant associated with the product concepts being tested.

In addition to the memory 220, the processor 210 can also be connected to at least one interface or other means for displaying, transmitting and/or receiving data, content or the like. In this regard, the interface(s) can include at least one communication interface 230 or other means for transmitting and/or receiving data, content or the like, as well as at least one user interface that can include a display 240 and/or a user input interface 250. The user input interface, in turn, can comprise any of a number of devices allowing the entity to receive data from a user, such as a keypad, a touch display, a joystick or other input device.

Figure 2:
FIG. 2 is a flow chart illustrating the process of conducting a prediction market for concept testing in accordance with embodiments of the present invention

Method of Conducting Prediction Markets for Concept Testing:

Referring now to FIG. 2, the operations are illustrated that may be taken in order to conduct a prediction market for testing product concepts in accordance with embodiments of the present invention. As shown, the process may begin at Block 201 when the Prediction Market server 32 (e.g., a processor executing thereon) causes an interface for accessing the Prediction Market system 30 to be displayed on a user's electronic device 10, 12, for example, via a website operated by the Prediction Market server 32.

In one embodiment, in order to display the interface to the user, the Prediction Market server 32 may transmit a message (e.g., an email, text message, etc.) to the user's electronic device 10, 12 informing the user of the possibility of participating in a prediction market and including a link through which the interface can be accessed (e.g., a link to the website operated by the Prediction Market server 32).

In one embodiment, only users who have been invited by another trader or by a merchant, in association with which a prediction market is being conducted, may participate in a prediction market. In particular, according to one embodiment, existing traders may be incentivized to invite additional traders by, for example, providing the existing trader with virtual credits for each new user invited and/or each invited user who actually participates in a prediction market. Alternatively, or in addition, a merchant may provide a list of potential traders it recommends or requests inviting to participate in a prediction market. In either embodiment, only potential users who have been identified by other traders or by a merchant may receive the message from the Prediction Market server 32.

According to one embodiment, the interface displayed to the user (via his or her electronic device) may first enable the user to establish a profile including, for example, a unique username and password to be used when accessing the prediction markets, as well as a physical mailing address associated with the user. The new user may be required to provide a physical mailing address, for example, so that the Prediction Market system 30 can prevent multiple account registrants (i.e., multiple participants registering the same physical address).

In one embodiment the new user may also be asked to provide a unique "invitation code." According to this embodiment, the invitation code may enable the Prediction Market system 30 to track how each participant came to participate in the prediction markets, as well as more easily identify colluders and participants who register multiple times. In particular, since colluders will likely have "closely related" invitation codes with just one or two degrees of separation, if the Prediction Market system 30 notices that closely related participants are bidding up a particular share, that may be a sign of collusion.

If the user is a returning or existing trader, the interface may include a place where the user can input his or her previously established unique username and password. In either event (i.e., whether a new trader or an existing trader), the process may continue, at Block 202, when the Prediction Market server 32 receives the trader's unique username and password and enables access to the Prediction Market system 30.

In one embodiment, once access is enabled, a brief description and tutorial of the Prediction Market system 30 may be provided to the new user, such as the one shown in FIGS.

3C-3E. Otherwise, the user may immediately begin taking steps to participate in a prediction market.

Figure 3B:
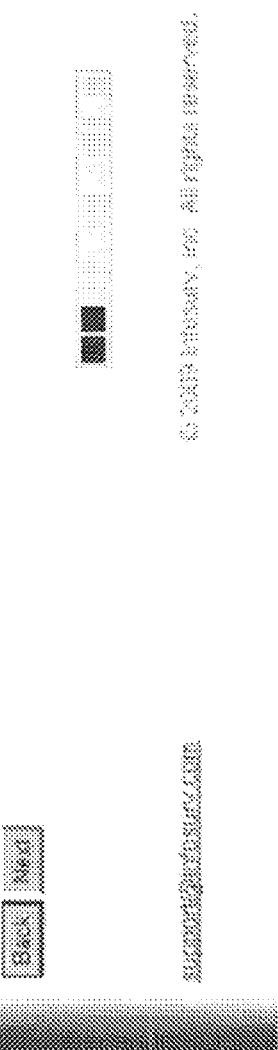
Figure 3D:
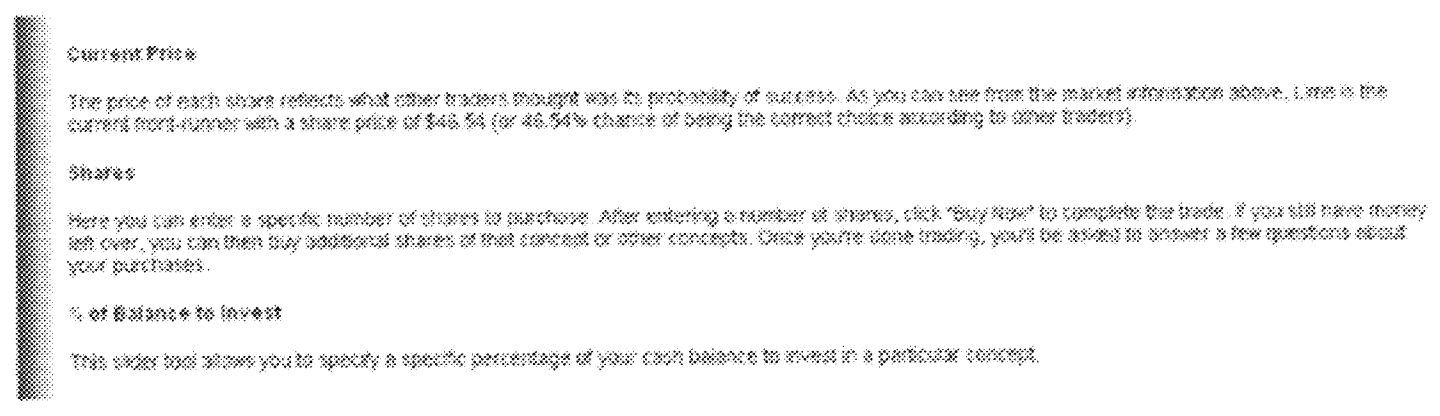
Figure 3E:
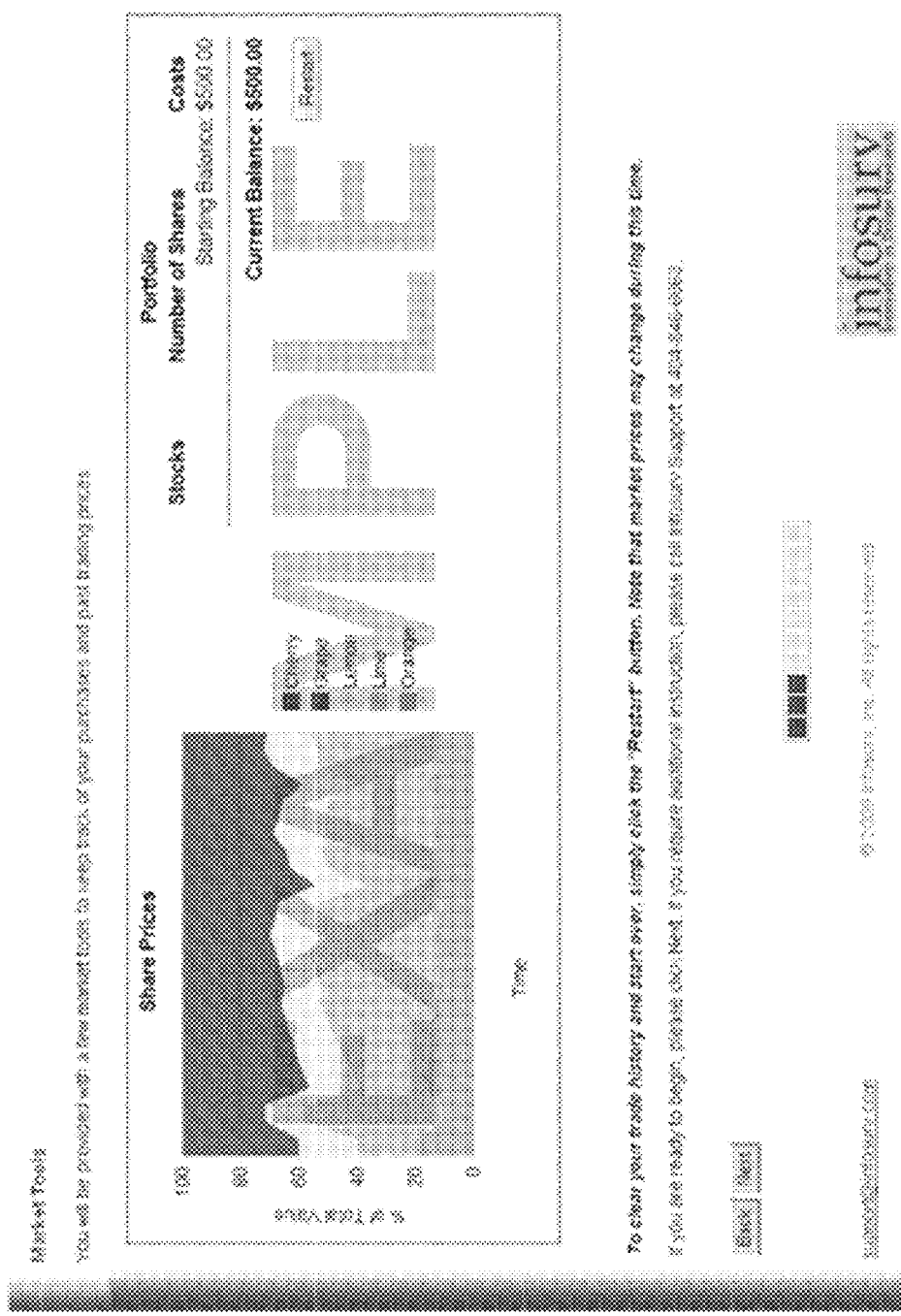

To that end, the Prediction Market server 32 (e.g., a processor executing thereon) may, at Block 203, display a request for the user to select a market in which he or she would like to participate as a trader and, in response, receive a selection of one or more markets from the trader. In one embodiment, the markets may include, for example, apparel, electronics, cosmetics and personal care, food and beverage, house and home, office supplies, pet services and supplies, sporting goods, toys and games, and/or the like. A user may select any one or more of the markets in which he or she feels he or she is most comfortable predicting whether a consumer will prefer a given product concept. An example of an interface through which the user may select one or more markets is shown in FIGS. 3A and 3B.

Figure 3F:
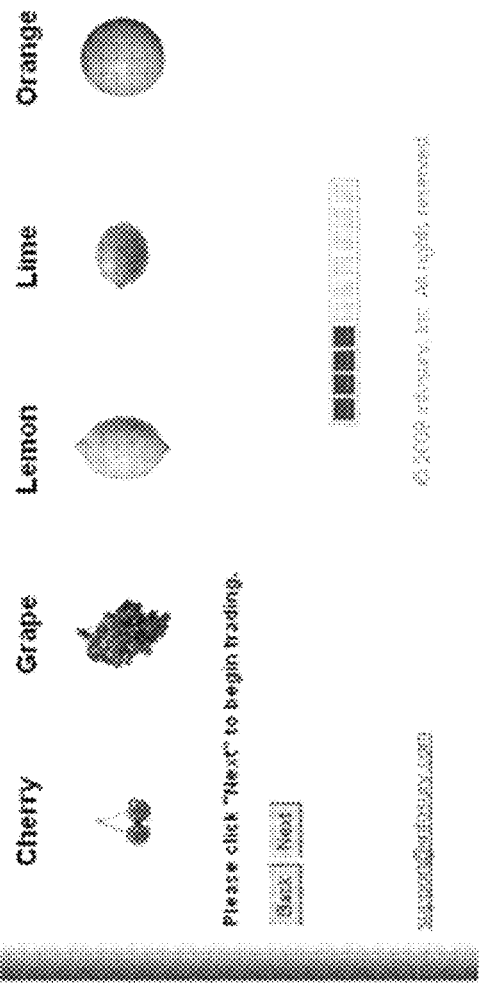
Figure 31:
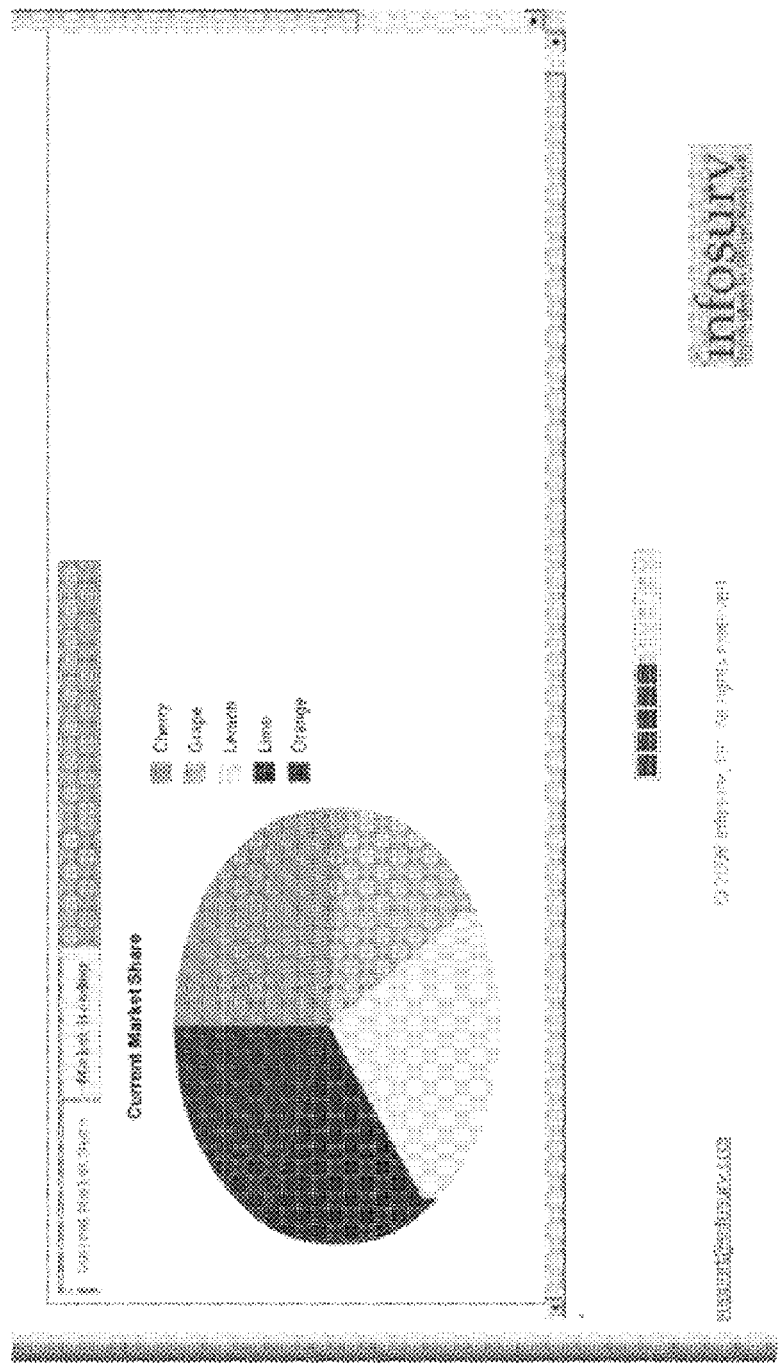

Upon receipt of the user's selected market(s), the Prediction Market server 32 (e.g., a processor executing thereon) may, at Block 204, retrieve and cause to be displayed information associated with each of a group of two or more product concepts falling within one of the selected markets. In one embodiment, this may involve retrieving, for example, from the concept database 36 and/or via a request to the corresponding merchant server 40, 42, a list of the product concepts to be tested in a single prediction market, and a description and/or image of each product concept in the group. As noted above, a "product concept" may include any product, package, logo, advertisement and/or the like for which a prediction market may be conducted in order to predict consumer preference. As an example, the Prediction Market server 32 may retrieve information associated with a number (e.g., five) of different sodas (e.g., lemon, lime, grape, cherry and orange) a company is thinking about launching. An example of the information that may be displayed is shown in FIG. 3F.

In addition to retrieving a description and/or image of the product concepts in the group, the Prediction Market server 32 (e.g., processor executing thereon) may retrieve, or determine, a current stock price associated with each product concept in the group and further cause this information to be displayed. In one embodiment, the sum of the prices of all the concepts in the group may equal some constant (e.g., $100), wherein, as described in more detail below, the price of each individual share may fluctuate up and down as traders make purchases.

In one embodiment, the group of product concepts to be presented to the trader (i.e., the prediction market in which the trader is invited to participate) may be selected based on a number of different factors including, for example, the make up of the traders already selected or identified to participate in a prediction market including that group of concepts. For example, according to one embodiment, traders may be invited to participate in a prediction market for a group of concepts based on demographic characteristics. To illustrate, it might be desirable to have a population of subjects that mirrors current census data relating to such factors as gender, income, race and/or the like. It might also be desirable to target a specific demographic segment.

At some point thereafter, the prediction market associated with the group of product concepts may be opened, wherein each trader invited to participate in that prediction market is enabled to purchase shares in whichever product concept(s) he or she thinks has the best chance of succeeding in the real marketplace or which other consumers will prefer. In one embodiment, the prediction market associated with a particular group of product concepts may not open until a certain number of traders have been selected or identified as participating in that market.

Figure 3G:
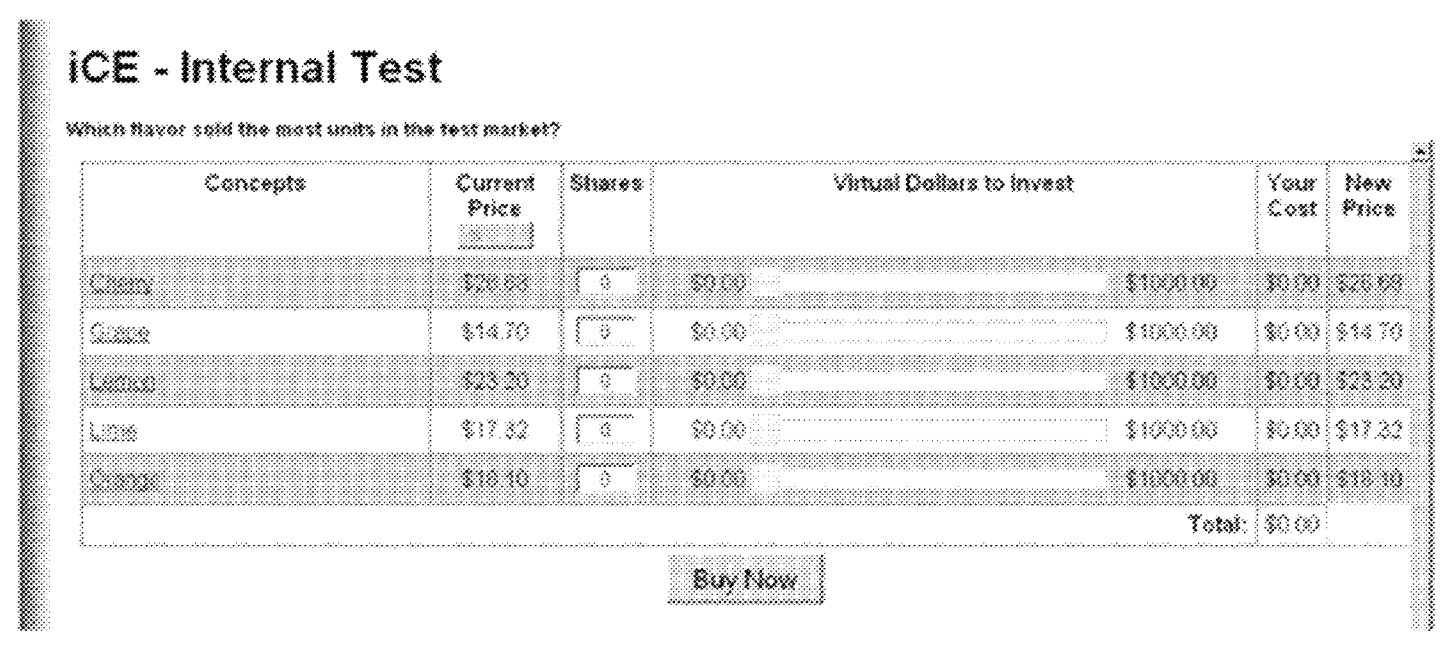
Figure 3H:
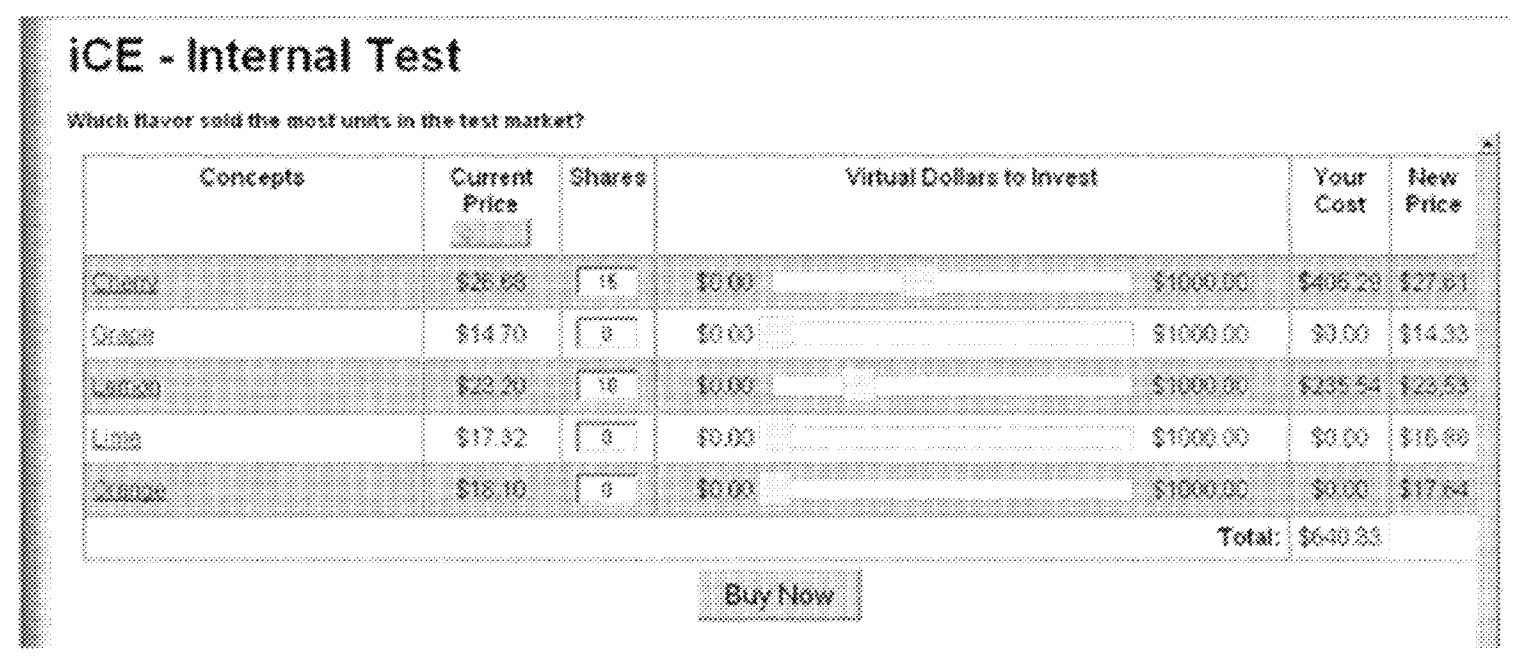

Once the prediction market has been opened, the process may continue when the trader indicates a number of shares he or she would like to purchase in one or more of the product concepts by, for example, moving a slide bar displayed on the interface in association with the product concept(s) in which he or she would like to purchase shares. An example of the interface through which the trader may purchase shares using a slide bar is shown in FIGS. 3G and 3H. The trader may purchase shares in only one product concept, or in multiple product concepts. The Prediction Market server 32 (e.g., a processor executing thereon) may, at Block 205, receive an indication of the shares being purchased.

In one embodiment, the Prediction Market server 32 (e.g., a processor executing thereon) may provide a recommendation of the number of shares the trader should purchase. In this embodiment, the Prediction Market server 32 may first receive an indication of how strongly the trader feels that the selected product concept will be successful. Then, based on that indication, the Prediction Market server 32 may indicate a recommended number of shares to purchase. For example, the Prediction Market server 32 may recommend more shares the more confident or strongly the trader feels that the selected product concept will be successful. In addition, in order to assist the trader in making his or her decision, an interface such as that shown in FIG. 3I, may be provided, wherein the current market share associated with each product concept is provided.

Assuming the trader has sufficient funds to purchase the shares indicated (as determined, for example, by accessing the trader database 34 and reviewing the trader's monetary balance), the Prediction Market server 32 (e.g., processor executing thereon) may, at Block 206, add an entry to the trader database 34 in association with the trader (e.g., the trader's unique username) indicating the number of shares purchased and the price(s) of those shares.

The Prediction Market server 32 and, in particular, a processor associated with the Prediction Market server 32 executing, for example, the price adjustment module, may then, at Block 207, alter or adjust the stock price of each product concept in the group of product concepts based on the number of shares purchased by the trader and in which product concept(s). The Prediction Market server 32 may further update the display accordingly (see FIG. 3H "New Price")). In one embodiment, adjusting the stock prices may involve, for example, increasing the stock price of the product concept(s) in which shares were purchased by a first amount that is based on the number of shares purchased and, correspondingly, decreasing the stock price of the remaining product concepts in the group of product concepts (i.e., those for which shares were not purchased) by a second amount, wherein the first amount multiplied by the number of product concepts in which shares were purchased is equal to the second amount multiplied by the number of remaining product concepts. In one embodiment the greater the number of shares purchased in one concept, the higher the price of that stock, and, as a result, the lower the price of the stock in the remaining concepts in the group.

To illustrate, assume for example, that there are five different product concepts in the group of product concepts (e.g., five different sodas—lemon, lime, grape, cherry and orange), and that the sum of the stock prices of each product concept in the group begins and remains at $100, such that the price of stock in each concept began at $20 (5 concepts.times.$20/concept=$100). If a trader purchases, for example, 10 shares in the grape soda, the price of the grape soda stock may increase by, for example, $8 (i.e., the first amount) to $28/share. Because the sum of the stock prices associated with all of the concepts in the group remains $100, the stock price in each of the remaining four sodas will decrease by $2 (i.e., the second amount equal to the first amount ($8) divided by the number of remaining product concepts (4)) to $18/share.

Figure 3J:
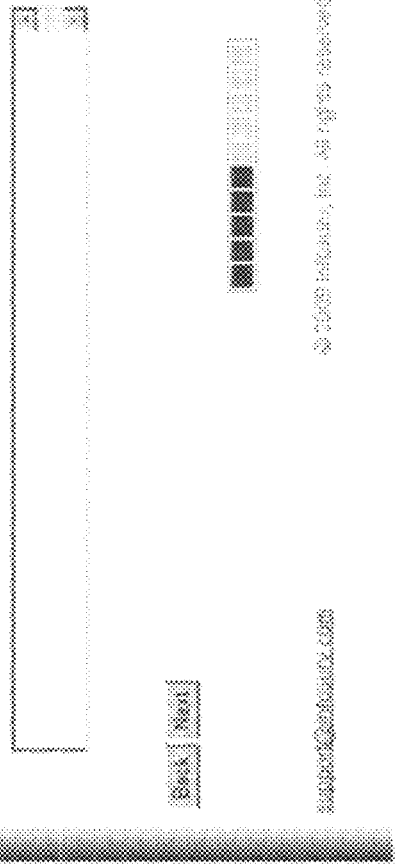
Figure 3K:
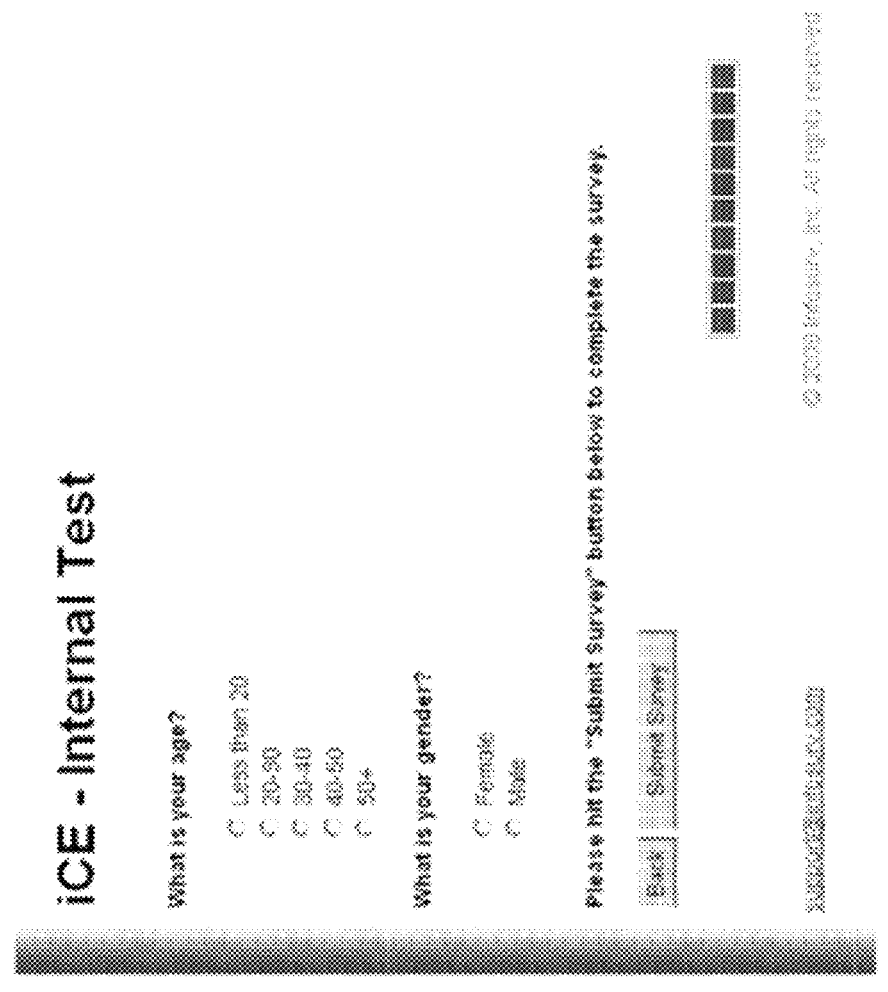

In addition to receiving stock purchase information from the trader, the Prediction Market server 32 of one embodiment may, for example, display and receive answers to one or more questions, wherein the answers may be used to enhance the feedback provided to a merchant regarding the prediction market in which the trader participated. (Block 208). Questions may include, for example, the trader's age, gender, race, occupation, salary, reasons for purchasing the shares purchased, and/or the like. FIGS. 3J and 3K provide examples of an interface through which the questions may be displayed and answers received.

At some point thereafter, the Prediction Market server 32 may "close the market," or prohibit traders from purchasing or selling any more shares in the product concepts in the group. (Block 209). In one embodiment, this may occur when a certain number of traders have made a trade within the group, after a certain time period has passed, after a certain number of overall shares have been purchased, and/or the like. In one embodiment, a trader may be notified (e.g., via an email, text message, or similar message, sent to or displayed for the user) of when it is anticipated that the market will close, such that the trader may make changes to his or her purchases up to the last moment.

Once the market is closed, the Prediction Market server 32 (e.g., a processor associated with the Prediction Market server 32 executing, for example, a winning concept module) may, at Block 210 identify the winning product concept from among the group of product concepts. In one embodiment, a separate group of users (i.e., users who did not participate in the prediction market for this group of concepts) may have been asked to identify which of the concepts in the group he or she thought consumers would prefer. The results of this survey may determine the winner of the prediction market. In this embodiment, a user may participate in a prediction market for one group of concepts while participating in a survey associated with another group of concepts. In another embodiment, the winning concept may be based on real life test market results. In this embodiment, some of the prediction markets (e.g., one half) may have a winning concept based on real life test market results, while others (e.g., the other one half) may be "un-resolvable," or may not have a winner at all. A trader may not know whether he or she is participating in a resolvable or an un-resolvable market. If he or she participates in an un-resolvable market, he or she may be given a refund of the amount spent purchasing stock, as well as some amount of virtual money to use in subsequent prediction markets. If the user participates in a resolvable market, he or she may be "cashed out," which is described below.

Once a winning concept has been identified, the Prediction Market server 32 and, in particular, a processor associated with the Prediction Market server 32 and executing, for example, a cash out module, may "cash out" the traders participating in the closed prediction market. (Block 211). In one embodiment, this may involve first determining the amount to be paid to (or added to the accounts of) each of the winning traders and the amount to be paid by (or deducted from the accounts of) the losing traders. This may be done, for example, by assuming that the value of each share in the winning product concept (i.e., each winning share) is now $100, while the value of each share in the losing product concepts (i.e., each losing share) is now $0. For traders who purchased a winning share, for each share purchased, the winning trader would be entitled to $100 minus the amount for which he or she purchased that share (since the share is now worth more than the trader paid for it). For traders who purchased a losing share, the purchase price (i.e., the number of shares purchased times the price per share at the time purchased) would be deducted from their funds (since the share is now worth less than the trader paid for it).

Cashing out may further include increasing or decreasing by the determined amount the funds associated with each trader stored in the trader database 32. In one embodiment, an email, text message and/or the like may be transmitted to each trader's electronic device notifying the trader of his or her earnings or losses associated with the closed prediction market. In one embodiment, the Prediction Market system 30 may further have a check generated and transmitted to each winning trader. In one embodiment, a minimum and maximum payout at a time may be established in order to prevent sending very small, or very large, checks.

In addition to cashing out participating traders, the Prediction Market server 32 (e.g., a processor associated with the Prediction Market server 32 executing, for example, an analysis module) may analyze the results of the prediction market and generate and transmit a report summarizing the analysis to the merchant associated with the product concepts in the group. (Block 212). In one embodiment, this may involve determining the final stock price of each concept (e.g., prior to converting to $100/$0 based on the winning concept), as well as the volume weighted average price (VWAP) associated with each concept.

As used herein, the VWAP may refer to the average price at which a share was purchased during the prediction market in association with a given product concept and can be considered by a merchant as the percentage likelihood the product concept will be successful. According to one embodiment, the VWAP can be calculated based on the price of the share each time it was purchased and the number of shares purchased. The following example illustrates how a VWAP may be calculated in accordance with embodiments described herein. Assume, for example, that User A purchased 10 shares of product concept X at $10/share; User B purchased 20 shares of product concept X at $12/share; User C purchased 5 shares of product concept X at $14/share, and User D purchased 5 shares of product concept X at $15/share, wherein User D was the last to purchase shares of the product concept before the prediction market was closed. In this example, the VWAP of product concept X is $12.13 ((10.times.$10)+(20.times.$12)+(5.times.$14)+(5.times.$15))/40=$12.13. According to embodiments of the present invention, this information may be more informative than merely providing the stock price of the product concept at the close of the market—or $15/share—since it better indicates how the average trader valued the shares of the product concept (i.e., how strongly each trader felt that the product concept would be successful).

According to one embodiment, the report may further include a summary of the traders who participated including their answers to the various questions posed at Block 208.

In one embodiment, the report may be transmitted to the merchant (i.e., to the merchant server 40, 42) in an email, or similar message. Alternatively, or in addition, the report may be accessible by the merchant via a website associated with the Prediction Market system 30.

In addition to the foregoing, according to embodiments of the present invention, the Prediction Market server may generate and transmit messages (e.g., emails, text messages, etc.) to a user (i.e., the user's computing device) regarding, for example, new markets a user may be interested in participating in based on the markets selected by the user and/or the prediction markets previously participated in by the user.

In one embodiment, a user may be playing for real money—i.e., a pay market. Alternatively, he or she may be purchasing shares as a game, with no real money changing hands—i.e., a non-pay market. In a pay market, in one embodiment, a non one-one exchange rate may be applied, wherein each U.S. dollar may be worth more than one virtual dollar. For example, each U.S. dollar may be worth $1000 in virtual money. In a non-pay market, a user may be given a virtual currency with no cash-in value. A non-pay market does not provide any cash incentive to a trader for participating. However, it allows the Prediction Market system 30 to evaluate how active each participating trader is in the process. A pay market, on the other hand, provides a tangible reward to the subject for participating.

In one embodiment a user may first be required to show a certain level of participation in a non-pay market before they are permitted to participate in a pay market.

In one embodiment, a user may be involuntarily dismissed from future participation in prediction markets via the Prediction Market system 30, for example, because he or she has not made a certain number of trades (e.g., one) within a certain time period (e.g., each month), or because he or she violated a rule associated with participating in the prediction markets (e.g., colluding with other market participants).

In one embodiment, the amount of money a trader is allowed to use to purchase shares in one or more product concepts in a single group may be capped in order to prevent "rich" traders from having too much influence in a given market.

In another embodiment, the number of traders permitted to participate in a given prediction market may be capped in order to prevent too many traders from crowding into an "easy" prediction market with an obvious right answer.

In yet another embodiment, in order to avoid and detect collusion amongst market participants in the form of one participant bidding on the same computer with multiple logins, the Prediction Market system 30 may further be configured to track the IP addresses of participants to assure the same one is not being used for multiple accounts.

As described above and as will be appreciated by one skilled in the art, embodiments of the present invention may be configured as a system, method or network entity. Accordingly, embodiments of the present invention may be comprised of various means including entirely of hardware, entirely of software, or any combination of software and hardware. Furthermore, embodiments of the present invention may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Embodiments of the present invention have been described above with reference to block diagrams and flowchart illustrations of methods, apparatuses (i.e., systems) and computer program products. It will be understood that each block of the block diagrams and flowchart illustrations, and combinations of blocks in the block diagrams and flowchart illustrations, respectively, can be implemented by various means including computer program instructions. These computer program instructions may be loaded onto a general purpose computer, special purpose computer, or other programmable data processing apparatus, such as processor 210 discussed above with reference to FIG. 1B, to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus (e.g., processor 210 of FIG. 1B) to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

As shown in FIGS. 4A-4J, one embodiment employs a market approach to making a medical diagnosis. This embodiment could use the collective knowledge of many different people to achieve a diagnosis regarding a medical condition using a decision market approach. The individuals participating could be people from a general population with many different backgrounds or they could be selected from a specific background. For example, all participants could be third year medical students, experienced nurses, or a combination of different types of health care professionals. One embodiment targets participants who are likely to be familiar with a wide range of symptoms. This could result in a smaller sample size being needed.

As shown in FIG. 4A, a participant is initially presented with an introduction screen that describes the task at hand and the queries if the participant would like to participate. If the participant indicates an intention to participant, then the screen shown in FIG. 4B is presented. This screen that queries the participant about his or her experience, including experience relating to various medical conditions and work experience. This screen may act as a gatekeeper that allows the market server (item 32 in FIG. 1A) to limit participants to those who have a desired background.

As shown in FIG. 4C, the next screen provides background information about the patient seeking a diagnosis and the next screen, as shown in FIG. 4D, provides the participant with instructions as to how to participate.

Figure 4E:
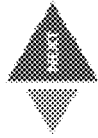

As shown in FIG. 4E, the participant is initially provided with an opportunity to give either a "thumbs up" or "thumbs down" vote for each of several potential diagnoses on a list or even to add a suggested diagnosis. If a participant provides a suggested diagnosis, then that suggested diagnosis will appear at the end of the list as it is viewed by successive participants. This feature might include an auto-complete feature that allows entry that allows entry only a preselected set of diagnoses (in one embodiment, wherein the most common diagnoses are presented first), thereby keeping the diagnosis format uniform and preventing spurious entries. This could also be accomplished with a pull-down menu of preselected diagnoses. Next, as shown in FIG. 4F, the participant is allowed to add information that might be useful to other participants in formulating a diagnosis. This could be part of an on-line forum, which allows questions (e.g., "have you tried . . . ?") and other comments that all participants can view.

Figure 4G:
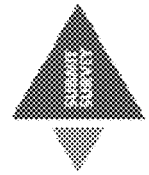
Figure 4I:
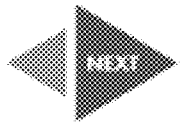

The next screen, as shown in FIG. 4G, queries the participant regarding personal information that can be used in classifying the participant. Once the participant has completed this screen, the participant's responses to the previous survey screens are submitted to the server.

The next screen, as shown in FIG. 4H, is presented to after the preliminary survey discussed in FIGS. 4A-4G has been completed by all participants. This screen presents a description of the task at hand and provides an incentive to participate. If the participant indicates a desire to participate, the participant is presented with the screen shown in FIG. 4I that shows the potential diagnoses that are deemed to be most likely by the system. At this point diagnostic suggestions described in FIG. 4E and voted on in that phase are selected for further review. In one representative embodiment, the system could select diagnostic suggestions that either (1) have "popularity" as determined by a net positive score (i.e., more "thumbs up" than "thumbs down"); or (2) have "controversy" as determined by a higher-than-average number of "thumbs up" even though its net score may be negative. Other methods of selecting diagnostic suggestions could also be employed. It could also show a list determined by a combination of several methods.

Figure 4J:
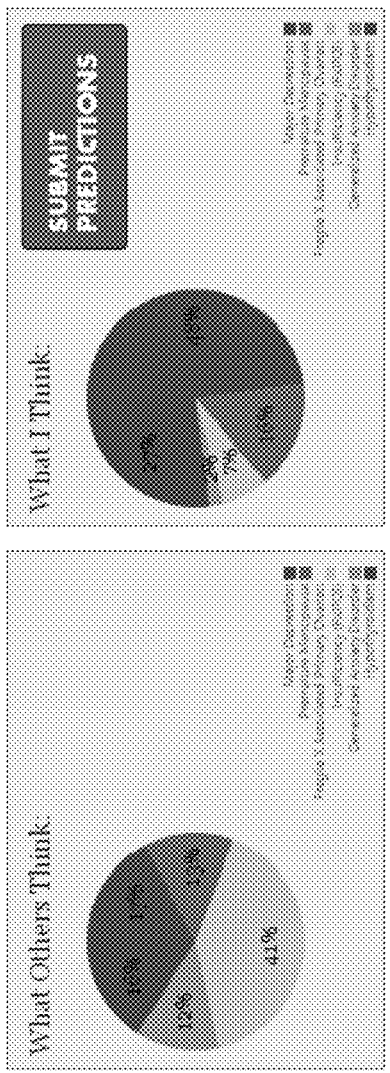

The participant is then presented with a market participation screen, as shown in FIG. 4J. This screen shows the participant the average of the current assessment of the other participants regarding each of the proposed diagnoses presented in the previous screen. It also allows the participant to input a likelihood of each diagnosis as a portion of the participant's "vote" by using sliding bars. The payout that the participant will get when one of his or her diagnoses is correct is also shown. (For example, in the example show, the participant gave "major depression" 48% of the vote. If that diagnosis is found to be correct, then the participant will receive $2.64 in payout. A graphical representation of the participant's vote is shown in a pie chart. Once the participant is satisfied with a particular combination of diagnosis weights, the participant clicks on a "submit predictions" button, which causes the participant's vote to be sent to the server.

Once all of the participant input has been collected, the patient receives a report that shows a volume-weighted average of the diagnoses that were voted on. The patient can take that report to a doctor, who may use it in formulating a diagnosis. The patent then inputs the doctor's final diagnosis into the system and this diagnosis is deemed to be the "correct" diagnosis, which is used in determining the payouts to the participants.

While not shown in the figures, one embodiment can include a rollover feature wherein when the participant points a cursor at a diagnosis, a link to an on-line encyclopedia (e.g., Wikipedia®) will be presented on the screen.

In one embodiment, potential patients could access the system via the global computer network. For example, when a potential patient enters a search relating to symptoms, advertisements for the system could appear in the result. In one embodiment, insurance companies could be charged for the potential patient to get access to the system. Because the system could result in fewer doctor visits in achieving a diagnosis, insurance companies would benefit from the system due to overall cost savings. In another embodiment, advertisers of related medical products could be charged for their advertisements appearing with the system screens. The participants could be benefited in several ways. For example, they could be given direct cash payouts for their participation. The system could also include a "leader board" that lists the participants with the most successful diagnoses. The system could give an added bonus or prizes to those at the top of the leader board, which would encourage more active participation by the participants. This system may be especially useful for diagnosing relatively rare ailments.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of generating a diagnosis of a medical condition experienced by a patient, comprising the steps of:
   (a) receiving, at a server in communication with a global computer network, a list of symptoms from a patient computer in communication with the global computer network, the symptoms relating to an ailment experienced by the patient;
   (b) presenting to a plurality of participants the list of symptoms on a corresponding plurality of participant computers in data communication with the server;
   (c) presenting to the plurality of participants a list of potential diagnoses corresponding to the list of symptoms to the plurality of participants on the plurality of participant computers;
   (d) receiving an input from each participant computer of each of the plurality of participants in which each input indicates a likelihood of each of the potential diagnoses being correct relative to each other diagnosis;
   (e) generating a volume weighted average of the inputs for each potential diagnosis, thereby generating a ranking of the potential diagnoses from highest likelihood of being correct to lowest likelihood of being correct;
   (f) transmitting the ranking from the server to the patient computer;
   (g) receiving at the server from the patient computer an indication of which of the potential diagnoses was found to be a correct diagnosis by a physician who examined the patient; and
   (h) paying a reward to each participant based on how likely the participant indicated that the correct diagnosis was correct.

2. The method of claim 1, further comprising the step of selecting participants for participation based on predefined criteria.

3. The method of claim 2, wherein the predefined criteria results in selected participants being health care professionals.

4. The method of claim 1, further comprising the steps of:
   (a) presenting to each of the participants a preliminary list of diagnoses;
   (b) receiving from each of the participants a vote regarding each of the diagnoses on the preliminary list; and (c) developing the list of potential diagnoses based vote of each participant.

5. The method of claim 1, further comprising the step of presenting a commenting forum that allows the participants to share information regarding diagnoses.

6. The method of claim 1, further comprising the step of presenting to each of the participants an indication of a current average input from each of the participants.

7. The method of claim 1, further comprising the steps of:
(a) allowing each of the participants to input a suggested diagnosis; and
(b) allowing each of the participants to vote on all suggested diagnoses.

8. The method of claim 7, wherein the step of allowing each of the participants to input a suggested diagnosis includes auto-completing input from a participant so as to limit the suggested diagnoses to a predefined set of diagnoses.

* * * * *